(12) United States Patent
Liu

(10) Patent No.: US 12,083,175 B1
(45) Date of Patent: Sep. 10, 2024

(54) ENHANCEMENT OF SELF-AMPLIFYING mRNA MOLECULES WITHIN LIPID NANOPARTICLES

(71) Applicant: Seqirus UK Limited, Berkshire (GB)

(72) Inventor: Hui Liu, Belmont, MA (US)

(73) Assignee: Seqirus UK Limited, Berkshire (GB)

( * ) Notice: Subject to any disclaimer, the term of this patent is extended or adjusted under 35 U.S.C. 154(b) by 0 days.

(21) Appl. No.: 17/340,460

(22) Filed: Jun. 7, 2021

Related U.S. Application Data

(60) Provisional application No. 63/036,027, filed on Jun. 8, 2020.

(51) Int. Cl.
*A61K 39/145* (2006.01)
*A61K 47/69* (2017.01)
*A61K 39/00* (2006.01)

(52) U.S. Cl.
CPC ........ *A61K 39/145* (2013.01); *A61K 47/6929* (2017.08); *A61K 2039/53* (2013.01)

(58) Field of Classification Search
None
See application file for complete search history.

(56) References Cited

U.S. PATENT DOCUMENTS

2022/0062409 A1* 3/2022 Capone .................. A61P 31/22

OTHER PUBLICATIONS

Cline et al., New Water-Soluble Phosphines as Reductants of Peptide and Protein Disulfide Bonds: Reactivity and Membrane Permeability, 2004, Biochemistry, vol. 43, pp. 15195-15203.*

* cited by examiner

*Primary Examiner* — Benjamin P Blumel
(74) *Attorney, Agent, or Firm* — Finnegan, Henderson, Farabow, Garrett & Dunner, LLP

(57) ABSTRACT

The present disclosure relates to methods of enhancing self-amplifying mRNA molecules (SAMs) encapsulated within lipid nanoparticles (LNPs). Specifically, enhancement of the stability, potency, and/or shelf-life of SAM/LNPs formulated in the presence of reducing agents is discussed.

29 Claims, 7 Drawing Sheets

ENHANCEMENT OF SELF-AMPLIFYING mRNA MOLECULES WITHIN LIPID NANOPARTICLES

This application claims priority to U.S. Provisional Application No. 63/036,027, filed Jun. 8, 2020, the contents of which are incorporated herein in their entirety.

FIELD

This invention is in the field of enhancement of self-amplifying mRNA molecules, in particular, when they are encapsulated within lipid nanoparticles (SAM/LNPs). The present disclosure relates to enhancing the stability, potency, and shelf-life of SAM/LNPs in the presence of a reducing agent.

BACKGROUND

Nucleic-acid based vaccines are an attractive approach to immunization. For instance, WO 2012/006369 discloses the use of self-replicating RNA molecules for immunization. WO 2012/031046 expands upon this notion by discussing the immunization potential of RNA within liposomes. WO 2016/037053 further elaborates upon this idea by discussing delivery of such biologically active agents as RNA to cells and tissues via lipid compounds.

It is an object of the invention to provide approaches to enhance self-amplifying mRNA molecules while encapsulated within lipid nanoparticles (SAM/LNPs). Specifically, the invention increases the stability, potency, and shelf-life of SAM/LNPs in the presence of a reducing agent relative to when reducing agents are absent.

SUMMARY

This invention generally relates to methods of enhancing the stability, potency, and shelf-life of self-amplifying mRNA molecules (SAMs) within lipid nanoparticles (LNPs) while in the presence of reducing agents and compositions of the same. The compositions of the invention may be immunogenic compositions, and the SAMs may encode polypeptides which comprise epitopes from influenza viruses.

The invention also provides a kit comprising a kit component that comprises SAM/LNPs in the presence of reducing agents.

The invention also provides methods for treating and/or preventing influenza virus disease and/or infection, methods for inducing an immune response against influenza virus, and methods for vaccinating a subject.

In a first embodiment, the epitopes encoded by the SAMs are influenza virus hemagglutinin epitopes.

In a second embodiment, the epitopes encoded by the SAMs are influenza A virus epitopes. In certain aspects of this embodiment, the epitopes encoded by the SAMs are influenza A virus hemagglutinin epitopes.

In a third embodiment, the epitopes encoded by the SAMs are influenza B virus epitopes. In certain aspects of this embodiment, the epitopes encoded by the SAMs are influenza B virus hemagglutinin epitopes.

In a fourth embodiment, the epitopes encoded by the SAMs are influenza B virus epitopes in the B/Yamagata/16/88-like lineage. In certain aspects of this embodiment, the epitopes encoded by the SAMs are influenza B virus hemagglutinin epitopes in the B/Yamagata/16/88-like lineage.

In a fifth embodiment, the epitopes encoded by the SAMs are influenza B virus epitopes in the B/Victoria/2/87-like lineage. In certain aspects of this embodiment, the epitopes encoded by the SAMs are influenza B virus hemagglutinin epitopes in the B/Victoria/2/87-like lineage.

DETAILED DESCRIPTION OF THE INVENTION

Figure 1:
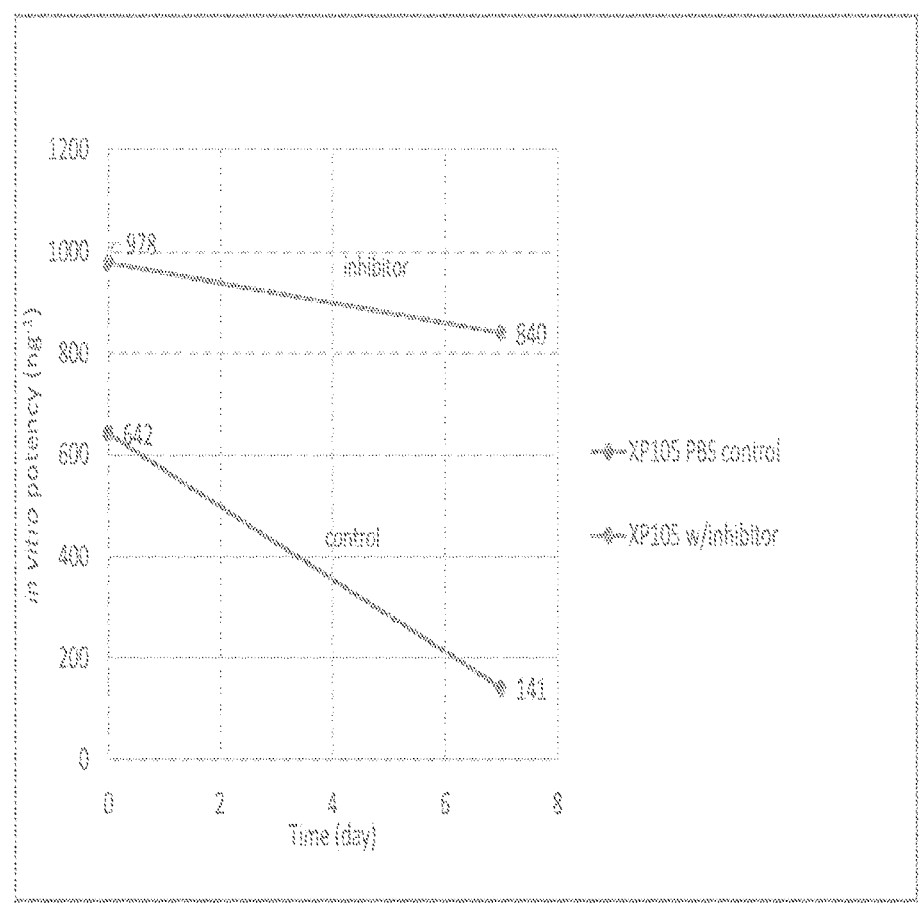
FIG. 1 depicts the stability of a lipid nanoparticle (LNP) comprising a self-amplifying mRNA molecule (SAM) in the presence or absence of an RNase inhibitor.

Many modifications and other embodiments of the disclosures set forth herein will come to mind to one skilled in the art to which these disclosures pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. Although specific terms are employed herein, they are used in a generic and descriptive sense only and not for purposes of limitation.

As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in the same manner as the term "comprising."

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition that "comprises," "has" or "includes" one or more features is not limited to possessing only those one or more features and can cover other unlisted features. The use of any and all examples, or exemplary language (e.g., "such as") provided with respect to certain embodiments herein is intended merely to better illuminate the present disclosure and does not pose a limitation on the scope of the present disclosure otherwise claimed.

Influenza Virus Antigens

Influenza virus has three types—A, B, and C. Influenza A virus is the most common flu virus infecting humans, animals, and birds. Influenza B virus infection mostly occurs in humans. Infection of influenza C virus does not cause any severe symptoms in human or mammals.

Influenza virus strains can change from season to season. In the current inter-pandemic period, seasonal trivalent vaccines include two influenza A strains (e.g., one H1N1 strain and one H3N2 strain) and one influenza B strain. Characteristics of a pandemic influenza strain are: (a) it contains a new hemagglutinin compared to the hemagglutinins in currently-circulating human strains, i.e., one that has not been evident in the human population for over a decade or has not been previously seen at all in the human population, such that the vaccine recipient and the general human population are immunologically naïve to the strain's hemagglutinin; (b) it is capable of being transmitted horizontally in the human population; and (c) it is pathogenic to humans. Pandemic strains are commonly H2, H5, H7 or H9 subtype influenza A virus strains, e.g., H5N1, H5N3, H9N2, H2N2, H7N1, and H7N7 strains. Within any subtype, a virus may fall into different clades.

Influenza A virus currently displays seventeen HA (hemagglutinin) subtypes: H1, H2, H3, H4, H5, H6, H7, H8, H9, H10, H11, H12, H13, H14, H15, H16, and H17. It also displays nine NA (neuraminidase) subtypes: N1, N2, N3, N4, N5, N6, N7, N8, and N9.

Influenza B virus currently does not display different HA subtypes, but influenza B virus strains do fall into two distinct lineages. These lineages emerged in the 1980s and have HAs which can be antigenically and/or genetically distinguished from each other (Rota et al. (1992) J Gen Virol 73:2737-42). Current influenza B virus strains are either B/Victoria/2/87-like or B/Yamagata/16/88-like. Strains in these two lineages are usually distinguished antigenically but differences in amino acid sequences have also been described for distinguishing them.

In some embodiments, the epitopes may be encoded by SAMs of the present invention. In particular, the epitopes may be influenza virus hemagglutinin epitopes. In some particular embodiments, the epitopes may be influenza A virus hemagglutinin epitopes. In some alternative embodiments, the epitopes may be influenza B virus hemagglutinin epitopes. In certain preferred embodiments, the SAMs may encode epitopes from both influenza A virus hemagglutinin and influenza B virus hemagglutinin. In particular embodiments, the SAMs may encode a polypeptide comprising epitopes from both influenza A virus hemagglutinin and influenza B virus hemagglutinin.

In embodiments where the epitopes are influenza A virus hemagglutinin epitopes, the epitopes may be H1 HA, H2 HA, H3 HA, H4 HA, H5 HA, H6 HA, H7 HA, H8 HA, H9 HA, H10 HA, H11 HA, H12 HA, H13 HA, H14 HA, H15 HA, H16 HA, or H17 HA epitopes.

In embodiments where the epitopes are influenza B virus hemagglutinin epitopes, the epitopes may be from a strain in the B/Victoria/2/87-like lineage or from a strain in the B/Yamagata/16/88-like lineage.

The Self-Amplifying mRNA Molecule

An immunogenic composition of the invention may include a SAM which encodes a polypeptide comprising an epitope from an influenza virus antigen. After administration to a subject, the SAM may be translated inside a cell to provide an influenza virus polypeptide in situ.

The SAM may be positive-stranded, so it can be translated within the cell without needing any intervening replicating steps such as reverse transcription. Advantageously, it may also bind to TLR7 receptors expressed by immune cells, thereby initiating an adjuvant effect. Preferred positive-stranded RNAs are self-replicating or self-amplifying. A SAM replicon may generate multiple daughter RNAs by self-transcription (via an antisense copy generated from itself). A SAM may thus typically be a positive-strand molecule which can be directly translated after delivery to a cell, and this translation may provide an RNA-dependent RNA polymerase which then produces both antisense and sense transcripts from the delivered SAM. Thus, the delivered SAM may lead to the production of multiple daughter SAMs. These daughter SAMs, as well as collinear subgenomic transcripts, may be translated themselves to provide in situ expression of one or more encoded polypeptides, or may be transcribed to provide further transcripts with the same sense as the delivered SAM which are translated to provide in situ expression of the polypeptide. The overall results of this sequence of transcription is an amplification in the number of the introduced replicon RNAs and so the encoded polypeptide becomes a major polypeptide product of the cells.

One suitable system for achieving self-replication may be to use an alphavirus-based RNA replicon. These positive-stranded replicons are translated after delivery to a cell to provide replicase (or replicase-transcriptase). The replicase may be translated as a polyprotein which auto-cleaves to provide a replication complex which creates genomic-strand copies of the positive-strand RNA. These negative-strand transcripts may themselves be transcribed to provide further copies of the positive-stranded parent RNA and also provide a subgenomic transcript which encodes the polypeptide. Translation of the sub genomic transcript thus may lead to in situ expression of the polypeptide by the infected cell. Suitable alphavirus replicons may use a replicase from a sindbis virus, a semliki forest virus, an eastern equine encephalitis virus, a Venezuelan equine encephalitis virus (VEEV), etc. Mutant or wild-type virus sequences may be used e.g. the attenuated TC83 mutant of VEEV has been used in replicons (WO 2005/113782).

A preferred SAM may thus encode (i) a RNA-dependent RNA polymerase which can transcribe RNA from the SAM and (ii) the polypeptide(s) of interest. The polymerase may be an alpha virus replicase e.g. comprising one or more of alphavirus non-structural proteins nsP1, nsP2, nsP3 and nsP4.

Whereas natural alphavirus genomes encode structural virion proteins in addition to the non-structural replicase polyprotein, it is preferred that a SAM of the invention does not encode alphavirus structural proteins. Thus, a preferred SAM may lead to the production of genomic RNA copies of itself in a cell, but not to the production of RNA-containing virions. The inability to produce these virions means that, unlike a wild-type alphavirus, the SAM cannot perpetuate itself in infectious form. The alphavirus structural proteins which are necessary for perpetuation in wild-type viruses are absent from SAMs of the invention and their place is taken by gene(s) encoding the polypeptide(s) of interest, such that the sub genomic transcript encodes the polypeptide(s) rather than the structural alphavirus virion proteins.

Thus, a SAM useful with the invention may have two open reading frames. The first (5') open reading frame encodes a replicase; the second (3') open reading frame encodes a polypeptide. In some embodiments the RNA may have additional (e.g. downstream) open reading frames e.g. to encode further polypeptides or to encode accessory polypeptides.

A SAM may have a 5' sequence which is compatible with the encoded replicase.

The SAM may be derived from or based on a virus other than an alphavirus, in particular, a positive-stranded RNA virus, and particularly a picornavirus, flavivirus, rubivirus, pestivirus, hepacivirus, calicivirus, or coronavirus. Alphaviruses are preferred, though, and suitable wild-type alphavirus sequences are well-known and are available from sequence depositories, such as the American Type Culture Collection. Representative examples of suitable alphaviruses include Aura (ATCC VR-368), Bebaru virus (ATCC VR-600, ATCC VR-1240), Cabassou (ATCC VR-922), Chikungunya virus (ATCC VR-64, ATCC VR-1241), Eastern equine encephalomyelitis virus (ATCC VR-65, ATCC VR-1242), Fort Morgan (ATCC VR-924), Getah virus (ATCC VR-369, ATCC VR-1243), Kyzylagach (ATCC VR-927), Mayaro (ATCC VR-66), Mayaro virus (ATCC VR-1277), Middleburg (ATCC VR-370), Mucambo virus (ATCC VR-580, ATCC VR-1244), Ndumu (ATCC VR-371), Pixuna virus (ATCC VR-372, ATCC VR-1245), Ross River virus (ATCC VR-373, ATCC VR-1246), Semliki Forest (ATCC VR-67, ATCC VR-1247), Sindbis virus (ATCC VR-68, ATCC VR-1248), Tonate (ATCC VR-925), Triniti (ATCC VR-469), Una (ATCC VR-374), Venezuelan equine encephalomyelitis (ATCC VR-69, ATCC VR-923, ATCC VR-1250 ATCC VR-1249, ATCC VR-532), Western equine encephalomyelitis (ATCC VR-70, ATCC VR-1251, ATCC VR-622, ATCC VR-1252), Whataroa (ATCC VR-926), and Y-62-33 (ATCC VR-375). Chimeric alphavirus replicons which include components from multiple different alphaviruses may also be useful.

SAMs may have various lengths but they are typically 5,000-25,000 nucleotides long, e.g. 8,000-15,000 nucleotides, or 9,000-12,000 nucleotides. Thus, the SAM may be longer than typical siRNAs delivered into cells.

A SAM useful with the invention may have a 5' cap (e.g. a 7-methylguanosine). This cap may enhance in vivo translation of the SAM.

The 5' nucleotide of a SAM useful with the invention may have a 5' triphosphate group. In a capped SAM, this may be linked to a 7-methylguanosine via a 5'-to-5' bridge. A 5' triphosphate may enhance RIG-I binding and thus promote adjuvant effects.

The SAM may have a 3' poly-A tail. It may also include a poly-A polymerase recognition sequence (e.g. AAUAAA) near its 3' end.

A SAM useful with the invention will typically be single-stranded. Single-stranded SAMs may generally initiate an adjuvant effect by binding to TLR7, TLR8, RNA helicases and/or PKR. A SAM delivered in double-stranded form (dsRNA) may bind to TLR3, and this receptor may also be triggered by dsRNA which is formed either during replication of a single-stranded mRNA molecule or within the secondary structure of a single-stranded mRNA molecule.

A SAM useful with the invention may conveniently be prepared by in vitro transcription (IVT). IVT may use a (DNA) template created and propagated in plasmid form in bacteria or created synthetically (for example by gene synthesis and/or polymerase chain reaction (PCR) engineering methods). For instance, a DNA-dependent RNA polymerase (such as the bacteriophage T7, T3 or SP6 RNA polymerases) may be used to transcribe the SAM from a DNA template. Appropriate capping and poly-A addition reactions may be used as required (although the replicon's poly-A is usually encoded within the DNA template). These RNA polymerases may have stringent requirements for the transcribed 5' nucleotide(s), and in some embodiments these requirements must be matched with the requirements of the encoded replicase to ensure that the IVT-transcribed RNA can function efficiently as a substrate for its self-encoded replicase.

As discussed in WO 2011/005799, the SAM may include (in addition to any 5' cap structure) one or more nucleotides having a modified nucleobase. For instance, a SAM may include one or more modified pyrimidine nucleobases, such as pseudouridine and/or 5-methylcytosine residues. In some embodiments, however, the SAM may not include any modified nucleobases and may not include any modified nucleotides, i.e., all of the nucleotides in the SAM may be standard A, C, G and U ribonucleotides (except for any 5' cap structure, which may include a 7'-methylguanosine). In other embodiments, the SAM may include a 5' cap comprising a 7'-methylguanosine, and the first 1, 2 or 3 5' ribonucleotides may be methylated at the 2' position of the ribose.

A SAM used with the invention ideally may include only phosphodiester linkages between nucleosides, but, in some embodiments, it may contain phosphoramidate, phosphorothioate, and/or methylphosphonate linkages.

The SAM may encode a polypeptide which comprises an epitope from an influenza virus antigen. The SAM preferably may encode a polypeptide comprising a fragment of an influenza virus hemagglutinin. It may encode a soluble cytosolic antigen, rather than a membrane-tethered or secreted antigen (although the cell may present the cytosolic antigen on the cell surface as part of immune processing). In situ expression of the polypeptide may elicit an anti-influenza immune response. For instance, it may lead to the production of antibodies which recognize an influenza virion, e.g., antibodies which bind to virion-surface hemagglutinin. Preferably, the elicited antibodies may be neutralizing or protective antibodies.

In some embodiments, the SAM may encode multiple polypeptides comprising epitopes from influenza virus antigens. In other embodiments, more than one SAM may encode different polypeptides comprising epitopes from one or more influenza virus antigens.

Lipid Nanoparticles

In some aspects of the invention, all or a portion of the SAMs may be attached (absorbed) to an outer surface of the LNP. In other aspects of the invention, all or a portion of the SAMs may be incorporated within the LNP. For example, all or a portion of the SAM may be incorporated within the lipids of the LNP. In preferred embodiments, all or a portion of the SAM may be encapsulated within the LNP, as disclosed in WO 2012/031046, the content of which is hereby incorporated by reference in its entirety. In certain aspects of the invention, the SAM may be separated from any external medium when encapsulated within the LNP. Encapsulation of the SAM within the LNP may protect the SAM from RNase digestion. The LNP may include some external SAMs (e.g. on its surface) but at least half of the SAMs may be encapsulated within the core of the LNP. Some aspects of the invention may comprise more than one LNP. In further aspects, each LNP may encapsulate one or more SAMs. For example, each LNP may encapsulate two SAMs. Alternatively, each LNP may encapsulate ten or more SAMs or one-hundred or more SAMs.

The LNP may efficiently deliver the SAM into the cytoplasm of the cell for in vivo expression of the encoded polypeptide(s). In certain embodiments, the SAM/LNP may be particularly useful for immunization. In certain preferred embodiments, the encapsulated SAM may encode one or more polypeptides of interest. In certain preferred embodiments, the polypeptide(s) of interest may include an influenza viral polypeptide. In preferred embodiments, the LNP may be a lipid particle or vesicle. In other embodiments, the LNP may be a liposome (e.g., a lipid monolayer, lipid bilayer, etc.). In certain embodiments, the LNP may be included in formulations or in vaccine compositions.

In some aspects, the invention may provide for a method of preparing a SAM/LNP under conditions that allow the LNP to encapsulate the SAM.

Various amphiphilic lipids may form bilayers in an aqueous environment to encapsulate the SAM within the LNP core. These lipids may have an anionic, cationic or zwitterionic hydrophilic head group. Suitable classes of phospholipid include, but are not limited to, phosphatidylethanolamines, phosphatidylcholines, phosphatidylserines, and phosphatidyl-glycerols. Useful cationic lipids include, but are not limited to, dioleoyl trimethylammonium propane (DOTAP), 1,2-distearyloxy-N,N-dimethyl-3-aminopropane (DSDMA), 1,2-dioleyloxyN, Ndimethyl-3-aminopropane (DODMA), 1,2-dilinoleyloxy-N,N-dimethyl-3-aminopropane (DlinDMA), 1,2-dilinolenyloxy-N,N-dimethyl-3-aminopropane (DLenDMA), 1,2-di-O-octadecenyl-3-trimethylammonium propane (DOTMA), DIMRIE, 2,5-bis((9Z, 12Z)-octadeca-9,12-dien-1-yloxy)benzyl 4-(dimethylamino)butanoate, KC2 and MC3. Zwitterionic lipids include, but are not limited to, acyl zwitterionic lipids and ether zwitterionic lipids. Examples of useful zwitterionic lipids include DMPC, DMPE, DPPE, DSPE, DPPC, DOPC, DSPC, dodecylphosphocholine, 1,2-dioleoyl-sn-glycero-3-phosphatidylethanolamine (DOPE), and 1,2-diphytanoyl-sn-glycero-3-phosphoethanolamine (DPyPE). The lipids in the LNPs of the invention may be saturated or unsaturated. The use of at least one unsaturated lipid for preparing LNPs is preferred. If an unsaturated lipid has two tails, both tails can be unsaturated, or the lipid can have one saturated tail and one unsaturated tail. A lipid can include a steroid group in one tail, e.g., as in RV05. LNPs of the invention may be formed from a single lipid or, more usually, from a mixture of lipids. A mixture may comprise (i) a mixture of cationic lipids, (ii) a mixture of anionic lipids and cationic lipids, (iii) a mixture of zwitterionic lipids and cationic lipids, or (vii) a mixture of anionic lipids, cationic lipids and zwitterionic lipids. Similarly, a mixture may comprise both saturated and unsaturated lipids. Where a mixture of lipids is used, not all of the component lipids in the mixture need to be amphiphilic, e.g., one or more amphiphilic lipids can be mixed with cholesterol.

An LNP of the present invention may include an amphiphilic lipid whose hydrophilic portion is PEGylated (i.e. modified by covalent attachment of a polyethylene glycol). This modification may increase stability and prevent non-specific adsorption of the LNP. PEG provides the LNP with a coat which may confer favorable pharmacokinetic characteristics. Various lengths of PEG may be used, e.g., between 0.5-8 kDa.

An LNP of the invention may be part of a composition comprising a plurality of lipid particles or vesicles, and the lipid particles or vesicles within the plurality may have a range of diameters. Diameters in a population may be measured using dynamic light scattering.

The Reducing Agent

In some aspects, the invention may comprise a SAM/LNP in media comprising a reducing agent.

In some aspects of the invention, the reducing agent may be tris(2-carboxyethyl)phosphine (e.g., TCEP). Alternatively, the reducing agent may be tri(2-methoxycarbonylethyl)phosphine (e.g., tmTCEP), tris(hydroxymethyl)phosphine (e.g., THMP), tris(hydroxypropyl)phosphine (THPP) or combinations thereof. In certain embodiments, the reducing agent may break (e.g., hydrolyze) disulfide bonds such as those present in RNase A. In preferred embodiments, TCEP functions as a better reducing agent for SAM stability relative to other reducing agents.

In preferred embodiments, "upstream" processing includes mixing a first fluid stream comprising the SAMs and a second fluid stream comprising a combination of lipids in a nanoassembler to provide a SAM/LNP formulation. The first fluid stream may include the SAMs and a reducing agent (e.g., 10.0 mM TCEP) in an appropriate buffer (e.g., citrate buffer). The second fluid stream may include a combination of lipids (e.g., a zwitterionic lipid, a cationic lipid, a pegylated lipid and cholesterol) dissolved in ethanol. In various embodiments, the reducing agent (e.g., 10.0 mM TCEP) may also be present in the second fluid stream. The presence of the reducing agent during "upstream" processing may reduce or eliminate (either temporarily or permanently) RNases present in the first and/or second fluid streams to enhance the stability of the SAMs on or within the SAM/LNP. The SAM/LNP formulation may then be subjected to tangential flow filtration (TFF) such that the citrate buffer is removed and exchanged with cryobuffer. The water soluble TCEP is completely removed by the TFF filtration step, resulting in a SAM/LNP formulation that is substantially devoid of TCEP. In some aspects of the invention, the concentration of the reducing agent may be 1-20 mM. In some particular aspects, the concentration of the reducing agent may be 1-10 mM. In other aspects, the concentration of the reducing agent may be 10-20 mM. In certain preferred embodiments, the concentration of the reducing agent may be held constant at 10 mM.

In preferred embodiments, "downstream" processing includes re-introducing the reducing agent (e.g., TCEP) into the cryobuffer of the SAM/LNP formulation. For example, the reducing agent may be re-introduced into the cryobuffer at a concentration of 0.1 mM to 10 mM. More specifically, the reducing agent may be re-introduced at a concentration of 0.2 mM to 1 mM. In preferred embodiments, the reducing agent may be re-introduced at a concentration of 0.2 mM. In various embodiments, the reducing agent re-introduced into the cryobuffer does not enter (e.g., penetrate, diffuse into, etc.) the core of the SAM/LNP.

In a preferred embodiment, rather than removing all of the reducing agent during the TFF step and then re-introducing the reducing agent into the cryobuffer, the TFF step may allow a portion of the reducing agent present in the citrate buffer to remain in the final SAM/LNP formulation.

In certain embodiments, the SAM/LNP formulation in either the presence or absence of reducing agent in the cryobuffer may be referred to as a drug product.

In preferred aspects of the invention, the stability, potency, and/or shelf-life of the SAM/LNPs may increase when the reducing agent is present in the upstream or the upstream and downstream portions of the SAM/LNP formulation process as compared to the absence of reducing agent in the upstream or downstream portions of the formulation process. In some aspects of the invention, the stability, potency, and/or shelf-life of the SAM/LNPS may increase when the reducing agent is present in both the upstream and downstream SAM/LNP formulation steps, as discussed above, relative to when the reducing agent is only present in the upstream SAM/LNP formulation step. It should be appreciated that although a correlation may exist between stability, potency and shelf-life (e.g., good shelf-life may correlate with good potency), in various embodiments a SAM/LNP may exhibit a relatively low potency but relatively high stability.

In other aspects, the stability of the SAM concentration within the SAM/LNPs, the stability of the encapsulation efficiency of the SAM within the LNP, and/or the stability of the zeta potential of the SAM within the LNP may be enhanced when the reducing agent is present in the upstream or the upstream and downstream portions of the SAM/LNP formulation process (e.g., as compared to the absence of reducing agent in the upstream or downstream portions of the formulation process). In yet other aspects, the stability of the SAM concentration within the LNP, the stability of the encapsulation efficiency of the SAM within the LNP, and/or the stability of the zeta potential of the SAM within the LNP may be enhanced when the reducing agent is present in both the upstream and downstream SAM/LNP formulation steps, as discussed above, relative to when the reducing agent is only present in the upstream SAM/LNP formulation step.

In some aspects of the invention, the stability of the SAM/LNP may be defined by measuring its half-life. Specifically, measuring SAM/LNP half-life may comprise determining how long it takes for the potency of the SAM/LNP to be reduced by half. In some aspects, the half-life of the SAM/LNP may be defined as an acceptable endpoint for shelf-life. In certain aspects, SAM/LNPs formulated in the presence of a reducing agent such as TCEP (either upstream only or upstream and downstream) may be stable for at least 5 weeks at 4° C. In other aspects, the size of the SAM/LNPs and/or the zeta potential of the SAM/LNPs may be stable for at least 5 weeks at 4° C.

Encapsulation efficiency may be measured by established methods in the art, including via RiboGreen assay. For example, RNA fluorescence of a SAM/LNP sample measured in the absence of detergent (e.g., Triton X) indicates the concentration of free RNA (e.g., SAM not encapsulated within an LNP). The SAM/LNP sample may then be treated with detergent to disrupt the LNP and RNA fluorescence measured again to indicate the total concentration of RNA in the sample. Independent standard curves may then be plotted (e.g., with y-axis as fluorescence, and x-axis as RNA concentration) to determine the concentration of free RNA and total RNA in the SAM/LNP sample. Encapsulation efficiency may then be determined as the percent of encapsulated RNA/total RNA).

A zetasizer may be used to measure SAM/LNP size (e.g., via Dynamic Light Scatter), polydispersity index (e.g., size distribution) and zeta potential (e.g., charge in solution) by established methods in the art. In some aspects, the RNA concentration of the SAM/LNP may range from 40 to 80 µg/mL. More specifically, the RNA concentration may range from 50 to 60 µg/mL. In some aspects, the LNP size may range from 80 to 120 nm, or, preferably, from 80 to 100 nm. In some aspects, the SAM encapsulation efficiency within the LNP may range from 90 to 100%. More specifically, the SAM encapsulation efficiency within the LNP may be about 100%. In some aspects, the zeta potential may range from 20 to 40 mV, or, preferably, from 30 to 35 mV.

The Immunogenic Composition

Immunogenic compositions may include a pharmaceutically acceptable carrier in addition to a SAM/LNP and any delivery system. A thorough discussion of such carriers is available in Gennaro (2000) *Remington: The Science and Practice of Pharmacy*, 20th edition.

Pharmaceutical compositions of the invention may include the active component (RNA) in plain water (e.g. w.f.i.) or in a buffer, (e.g., a phosphate buffer, a Tris buffer, a borate buffer, a succinate buffer, a histidine buffer, or a citrate buffer). Buffer salts may be included in the 5-20 mM range.

Pharmaceutical compositions of the invention may have a pH between 5.0 and 9.5, e.g., between 6.0 and 8.0.

Compositions of the invention may include sodium salts (e.g. sodium chloride) to give tonicity. A concentration of 10±2 mg/ml NaCl is typical, e.g., about 9 mg/ml.

Compositions of the invention may include metal ion chelators. These can prolong RNA stability by removing ions which can accelerate phosphodiester hydrolysis. Thus, a composition may include one or more of EDTA, EGTA, BAPTA, pentetic acid, etc. Such chelators are typically present at between 10-500 µM, e.g., 0.1 mM. A citrate salt, such as sodium citrate, can also act as a chelator, while advantageously also providing buffering activity.

Pharmaceutical compositions of the invention may have an osmolality of between 200 mOsm/kg and 400 mOsm/kg, e.g., between 240-360 mOsm/kg, or between 290-310 mOsm/kg.

Pharmaceutical compositions of the invention may include one or more preservatives, such as thiomersal or 2-phenoxyethanol. Mercury-free compositions are preferred, and preservative-free vaccines may be prepared.

Pharmaceutical compositions of the invention are in particular sterile.

Pharmaceutical compositions of the invention are in particular non-pyrogenic, e.g., containing <1 EU (endotoxin unit, a standard measure) per dose, and particularly <0.1 EU per dose.

In certain embodiments, pharmaceutical compositions of the invention are gluten-free.

Pharmaceutical compositions of the invention may be prepared in unit dose form. In some embodiments, a unit dose may have a volume of between 0.1-1.0 mL e.g. about 0.5 mL.

A pharmaceutical composition of the invention may include one or more small molecule immunopotentiators. For example, the composition may include a TLR2 agonist (e.g. Pam3CSK4), a TLR4 agonist (e.g. an aminoalkyl glucosaminide phosphate, such as E6020), a TLR7 agonist (e.g. imiquimod), a TLR8 agonist (e.g. resiquimod) and/or a TLR9 agonist (e.g. IC31). Any such agonist ideally has a molecular weight of <2000 Da.

The compositions may be prepared as injectables, either as solutions or suspensions. The composition may be prepared for pulmonary administration e.g. by an inhaler, using a fine spray. The composition may be prepared for nasal, aural or ocular administration, e.g., as spray or drops. Injectables for intramuscular administration are typical.

Compositions may comprise an immunologically effective amount of a SAM/LNP, as well as any other components, as needed. By 'immunologically effective amount', it is meant that the administration of that amount to an individual, either in a single dose or as part of a series, may be effective for treatment or prevention. This amount varies depending upon the health and physical condition of the individual to be treated, age, the taxonomic group of the individual to be treated (e.g. non-human primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials. The RNA content of the SAM/LNP of compositions of the invention will generally be expressed in terms of the amount of RNA per dose. A preferred dose has ≤100 μg RNA (e.g. from 10-100 μg, such as about 10 μg, 25 μg, 50 μg, 75 μg or 100 μg). Expression can be seen at much lower levels (e.g.≤1 μg/dose, ≤100 ng/dose, ≤10 ng/dose, ≤ 1 ng/dose), but a minimum dose of 0.1 μg is preferred (see WO 2012/006369).

The invention may also provide a delivery device (e.g. syringe, nebulizer, sprayer, inhaler, dermal patch, etc.) containing a pharmaceutical composition of the invention. This device may be used to administer the composition to a subject.

Methods of Treatment and Medical Uses

Pharmaceutical compositions of the invention may be for in vivo use for eliciting an immune response against influenza virus.

The invention may provide a method for raising an immune response in a vertebrate comprising the step of administering an effective amount of a pharmaceutical composition of the invention. In certain embodiments, the immune response may be protective and, in certain aspects, involve antibodies and/or cell-mediated immunity. The method may raise a booster response.

The invention may also provide a pharmaceutical composition of the invention for use in a method for raising an immune response against influenza virus in a vertebrate.

The invention may also provide the use of a SAM/LNP as described above, in the manufacture of a medicament for raising an immune response against influenza virus in a vertebrate.

By raising an immune response in the vertebrate by these uses and methods, the vertebrate may be protected against influenza virus infection and/or disease. The compositions may be immunogenic, and, in certain embodiments, may be formulations or vaccine compositions. Vaccines according to the invention may either be prophylactic (i.e. to prevent infection) or therapeutic (i.e. to treat infection), but will typically be prophylactic.

The vertebrate may, in particular embodiments, be a mammal, such as a human or a large veterinary mammal (e.g. horses, cattle, deer, goats, pigs). Where the vaccine is for prophylactic use, the human may preferably be a child (e.g. a toddler or infant) or a teenager; where the vaccine is for therapeutic use, the human may preferably be a teenager or an adult. A vaccine intended for children may also be administered to adults, e.g. to assess safety, dosage, immunogenicity, etc.

Vaccines prepared according to the invention may be used to treat both children and adults. Thus, a human patient may be less than 1 year old, less than 5 years old, 1-5 years old, 5-15 years old, 15-55 years old, or at least 55 years old. Preferred patients for receiving the vaccines are the elderly (e.g. >50 years old, >60 years old, and particularly >65 years), the young (e.g. <5 years old), hospitalized patients, health care workers, armed service and military personnel, pregnant women, the chronically ill, or immunodeficient patients. The vaccines are not suitable solely for these groups, however, and may be used more generally in a population.

Compositions of the invention may generally be administered directly to a patient. Direct delivery may be accomplished by parenteral injection (e.g. subcutaneously, intraperitoneally, intravenously, intramuscularly, intradermally, or to the interstitial space of a tissue). Alternative delivery routes may include rectal, oral (e.g. tablet, spray), buccal, sublingual, vaginal, topical, transdermal or transcutaneous, intranasal, ocular, aural, pulmonary or other mucosal administration. Intradermal and intramuscular administration are two preferred routes. Injection may be via a needle (e.g. a hypodermic needle), but needle-free injection may alternatively be used. A typical intramuscular dose is 0.5 ml.

The invention may be used to elicit systemic and/or mucosal immunity, and, in particular, to elicit an enhanced systemic and/or mucosal immunity.

One way of checking efficacy of therapeutic treatment involves monitoring pathogen infection after administration of the composition. One way of checking efficacy of prophylactic treatment involves monitoring immune responses, systemically (such as monitoring the level of IgG1 and IgG2a production) and/or mucosally (such as monitoring the level of IgA production), against the antigen. Typically, antigen-specific serum antibody responses may be determined postimmunization. Another way of assessing the immunogenicity of the compositions may be to screen patient sera or mucosal secretions against a target polypeptide. A positive reaction between the protein and the patient sample may indicate that the patient has mounted an immune response to the polypeptide in question. The efficacy of the compositions may also be determined in vivo by challenging appropriate animal models of the pathogen of interest infection.

Dosage may be by a single-dose schedule or a multiple-dose schedule. Multiple doses may be used in a primary immunization schedule and/or in a booster immunization schedule. In a multiple dose schedule, the various doses may be given by the same or different routes, e.g., a parenteral prime and mucosal boost, a mucosal prime and parenteral boost, etc. Multiple doses may typically be administered at least 1 week apart (e.g. about 2 weeks, about 3 weeks, about 4 weeks, about 6 weeks, about 8 weeks, about 10 weeks, about 12 weeks, about 16 weeks, etc.). In one embodiment, multiple doses may be administered approximately 6 weeks, 10 weeks, and 14 weeks after birth, e.g., at an age of 6 weeks, 10 weeks, and 14 weeks, as often used in the World Health Organization's Expanded Program on Immunization ("EPI"). In an alternative embodiment, two primary doses are administered about two months apart, e.g. about 7, 8, or 9 weeks apart, followed by one or more booster doses about 6 months to 1 year after the second primary dose, e.g. about 6, 8, 10, or 12 months after the second primary dose. In a further embodiment, three primary doses are administered about two months apart, e.g. about 7, 8, or 9 weeks apart, followed by one or more booster doses about 6 months to 1 year after the third primary dose, e.g. about 6, 8, 10, or 12 months after the third primary dose.

Kits

The invention may also provide a kit comprising a kit component comprising a SAM/LNP which encodes one or more polypeptides that comprise an epitope(s) from an influenza virus antigen.

The SAM/LNP kit component may be in aqueous form or in solid or dry form (e.g. lyophilized). Suitable containers for the kit components may include, for example, bottles, vials, syringes, and test tubes. Containers may be formed from a variety of materials, including glass or plastic. A container may have a sterile access port (for example, the container may be an intravenous solution bag or a vial having a stopper pierceable by a hypodermic injection needle).

The kit may further comprise another container comprising a pharmaceutically acceptable buffer, such as phosphate-buffered saline, Ringer's solution, or dextrose solution. It may also contain other materials useful to the end-user, including other pharmaceutically acceptable formulating solutions such as buffers, diluents, filters, needles, and syringes, or other delivery device. The kit may further include a container comprising an adjuvant (such as an oil-in-water emulsion).

The kit may also comprise a package insert containing written instructions for methods of inducing immunity or for treating infections. The package insert may be an unapproved draft package insert or may be a package insert approved by the Food and Drug Administration (FDA) or other regulatory body.

One aspect of the invention may relate to the "prime and boost" immunization regimens in which the immune response induced by a priming composition is boosted by a boosting composition. For example, following priming (at least once) with an antigen (e.g., after administration of the self-replicating mRNA molecule), a boosting composition may comprise substantially a different form of the antigen. Administration of the boosting composition may generally be weeks or months after administration of the priming composition, such as about 1 week, about 2 weeks, about 3 weeks, about 4 weeks, about 8 weeks, about 12 weeks, about 16 weeks, about 20 weeks, about 24 weeks, about 28 weeks, about 32 weeks, about 36 weeks, about 40 weeks, about 44 weeks, about 48 weeks, about 52 weeks, about 1 month, about 2 months, about 3 months, about 4 months, about 5 months, about 6 months, about 7 months, about 8 months, about 9 months, about 10 months, about 11 months, about 12 months, about 18 months, about 2 years, about 3 years, about 4 years, about 5 years, about 6 years, about 7 years, about 8 years, about 9 years, or about 10 years after the priming composition is administered.

General

The term "comprising" may encompass "including" as well as "consisting," e.g., a composition "comprising" X may consist exclusively of X or may include something additional e.g. X+Y.

The term "about" in relation to a numerical value x is optional and means, for example, x±10%.

The word "substantially" does not exclude "completely," e.g., a composition which is "substantially free" from Y may be completely free from Y. Where necessary, the word "substantially" may be omitted from the definition of the invention.

An "epitope" may be a portion of an antigen that is recognized by the immune system (e.g., by an antibody, or by a T cell receptor). A polypeptide epitope may be linear or conformational. T-cells and B-cells recognize antigens in different ways. T-cells recognize peptide fragments of proteins that are embedded in class-II or class-I MHC molecules at the surface of cells, whereas B-cells recognize surface features of an unprocessed antigen, via immunoglobulin-like cell surface receptors. The difference in antigen recognition mechanisms of T-cells and B-cells may be reflected in the different natures of their epitopes. Thus, whereas B-cells recognize surface features of an antigen or a pathogen, T-cell epitopes (which comprise peptides of about 8-12 amino acids in length) may be "internal" as well as "surface" when viewed in the context of the three-dimensional structure of the antigen. Accordingly, a B-cell epitope may be preferably exposed on the surface of the antigen or pathogen, and may be linear or conformational, whereas a T-cell epitope may be typically linear but may not be required to be available or on the surface of the antigen. Normally, a B-cell epitope may include at least about 5 amino acids but may be as small as 3-4 amino acids. A T-cell epitope, such as a CTL epitope, may typically include at least about 7-9 amino acids, and a helper T-cell epitope may typically include at least about 12-20 amino acids.

All of the claims in the claim listing are herein incorporated by reference into the specification in their entireties as additional embodiments.

EXAMPLES

Example 1: The Presence of a Reducing Agent Increases the Stability, Potency, and Shelf-Life of SAM/LNPs Relative to SAM/LNPs Formed in the Absence of a Reducing Agent The upstream formulation step of the present invention includes providing two separate fluid streams which are combined/mixed using a nanoassembler. The first fluid stream includes SAMs (e.g., approximately 26 µg/ml) and approximately 10.0 mM TCEP in a citrate buffer. The second fluid stream includes a combination of four different types of lipids, including a cationic lipid (e.g., 2,5-bis((9Z,12Z)-octadeca-9,12-dien-1-yloxy)benzyl 4-(dimethylamino)butanoate), a zwitterionic lipid (e.g., 1,2-distearoyl-sn-glycero-3-phosphocholine (DSPC)), a PEGylated lipid (e.g., DMG-PEG2000) and cholesterol. In one embodiment, the volume ratio of the first and second streams may be 2:1. When the first and second fluid streams are mixed/combined by the nanoassembler, the negatively charged SAMs within the first fluid stream interact with the positively charged (e.g., cationic) lipids of the second fluid stream to form SAM/lipid complexes. The SAM/LNP complexes then interact with the remaining lipids of the second stream to form the SAM/LNPs. In various embodiments, the concentration of SAM within the SAM/LNP may be approximately 50 µm/ml. Due to the inherent presence of RNases in citrate buffer, the reducing agent (e.g., TCEP) prevents or reduces degradation of the SAM within the first fluid stream both before and during the SAM/LNP formulation step. Because TCEP is water soluble, and precipitates out in the presence of ethanol of the second fluid stream, it is unlikely that any TCEP (or at least any appreciable or measurable amount of TCEP) is incorporated on or within the SAM/LNPs.

The SAM/LNP formulation is then subjected to tangential flow filtration (TFF) such that the citrate buffer is removed and exchanged with cryobuffer. The 10.0 mM water soluble TCEP is completely removed by this TFF filtration step, resulting in SAM/LNPs that are devoid of TCEP.

The downstream formulation step, if performed, involves reintroducing the reducing agent (e.g., TCEP) into the cryobuffer at a desired amount, e.g., 0.2 mM, thereby removing or inactivating (either temporarily or permanently) any RNases that were not removed/inactivated during the upstream processing step and/or were introduced during the TFF step (e.g., present in the cryobuffer etc.). The SAM/LNP formulations in both the presence and absence of TCEP in the cryobuffer are then assessed for stability, potency, and shelf-life.

Figure 2A:
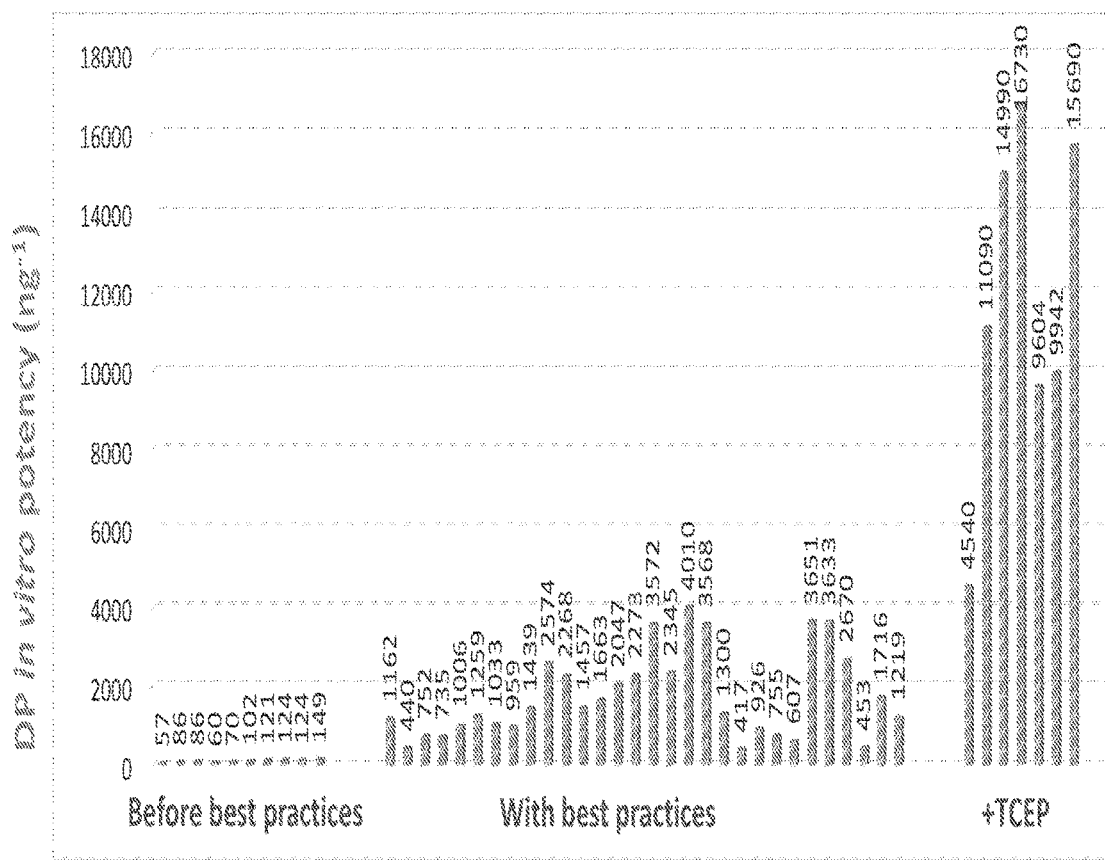
FIG. 2(a) depicts the potency of various LNPs comprising SAMs (SAM/LNPs) in the presence of the reducing agent TCEP.
Figure 2B:
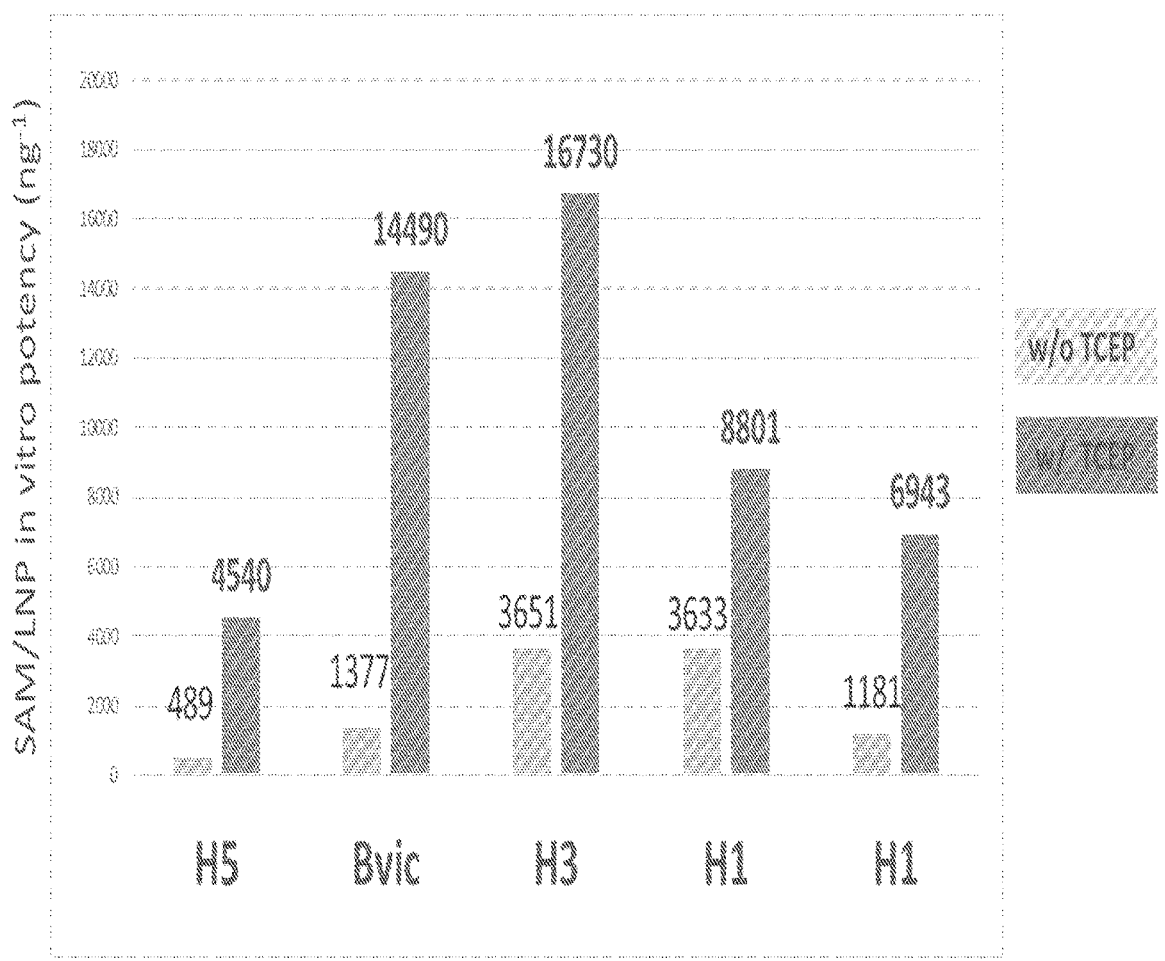
FIG. 2(b) depicts the potency of SAM/LNPs against various strains of influenza virus when in the presence or absence of TCEP.
Figure 3:
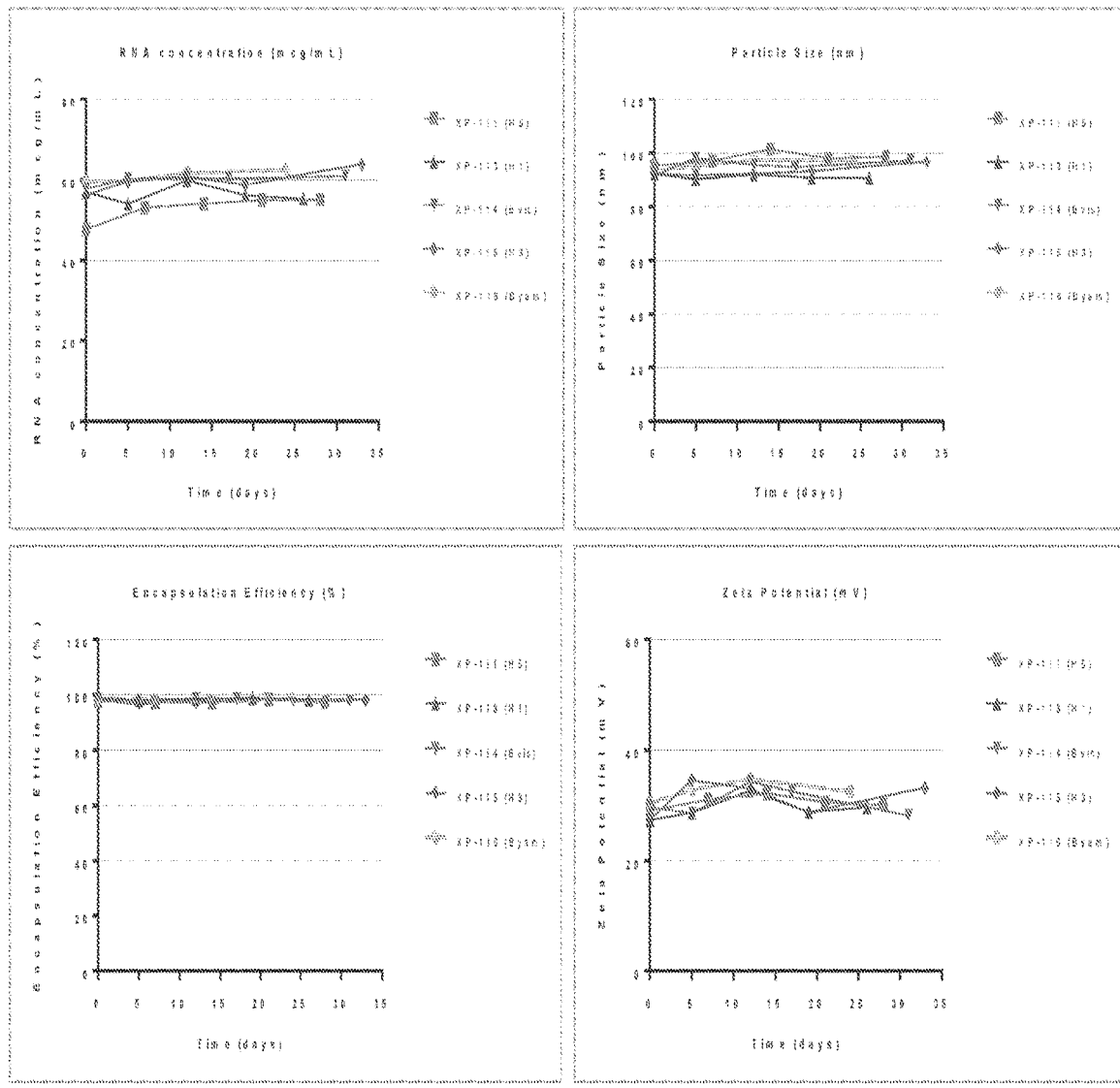
FIG. 3 depicts the stability of RNA concentration, particle size, encapsulation efficiency, and zeta potential of SAM/LNPs in the presence of TCEP at 4°C over a five-week period. As can be seen, the LNPs encapsulate SAMs that express hemagglutinin from various strains of influenza virus.
Figure 4:
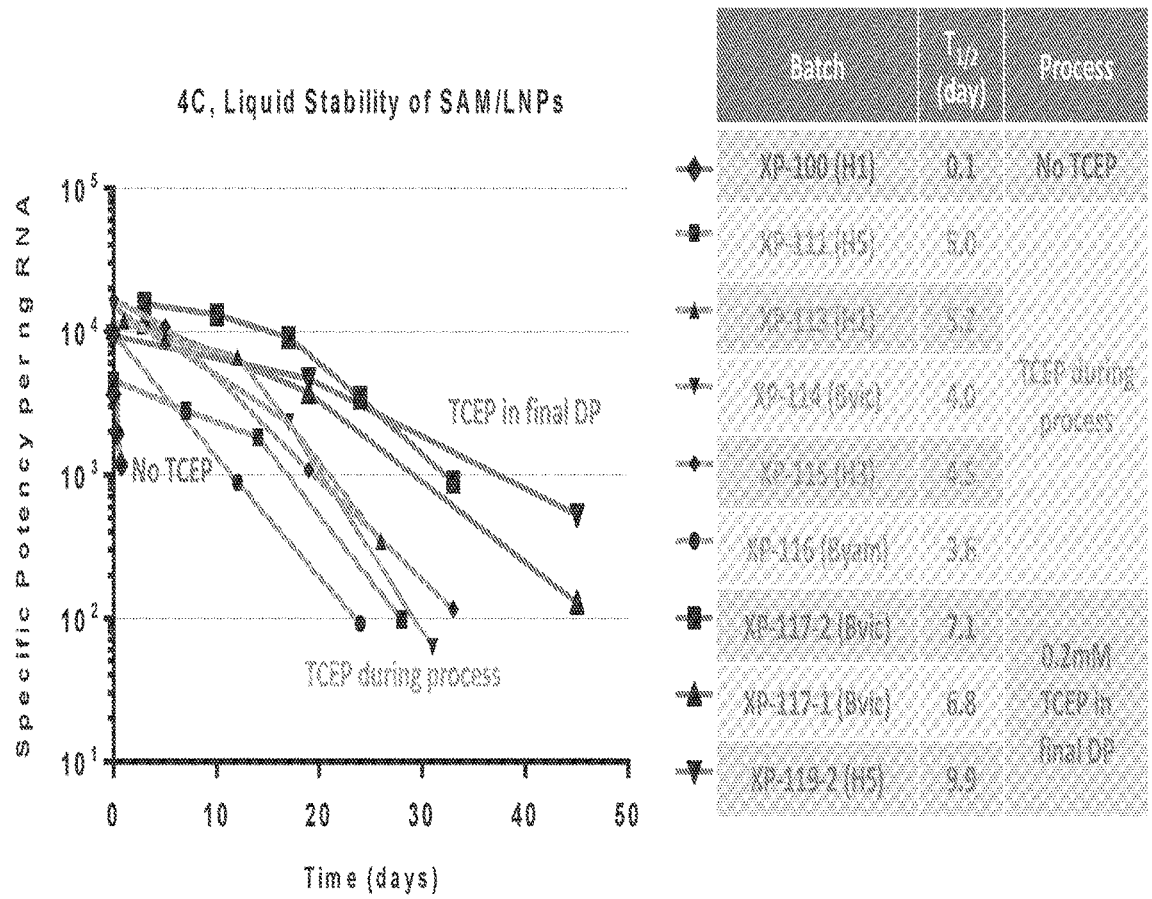
FIG. 4 depicts the potency, stability, and shelf-life of SAM/LNPs at 4° C. over a five-week period when (1) TCEP is present during formation of the SAM/LNPs and is re-introduced in the final SAM/LNP formulation ("upstream" and "downstream"; green-colored lines); (2) TCEP is present during formation of the SAM/LNPs but is not re-introduced in the final SAM/LNP formulation ("upstream only"; orange-colored lines), or (3) TCEP is absent throughout the SAM/LNP formulation process (red-colored lines).
Figure 5:
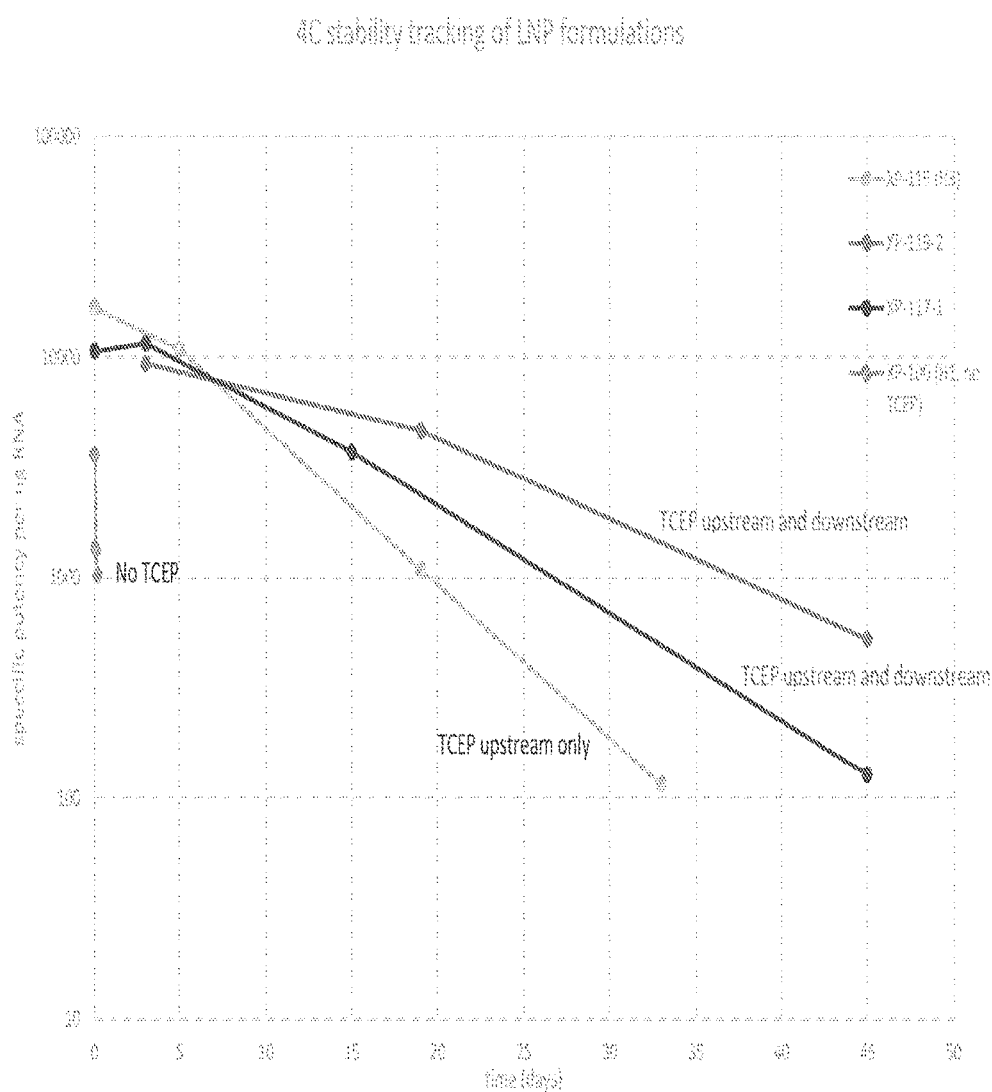
FIG. 5 depicts the stability and potency of SAM/LNPs when (1) TCEP is present during formation of the SAM/LNPs and is re-introduced in the final SAM/LNP formulation ("upstream" and "downstream"; red and purple-colored lines), (2) TCEP is present during formation of the SAM/LNPs but is not re-introduced in the final SAM/LNP formulation ("upstream only"; yellow-colored line), or (3) TCEP is absent throughout the LNP formulation process (green-colored line).
Figure 6A:
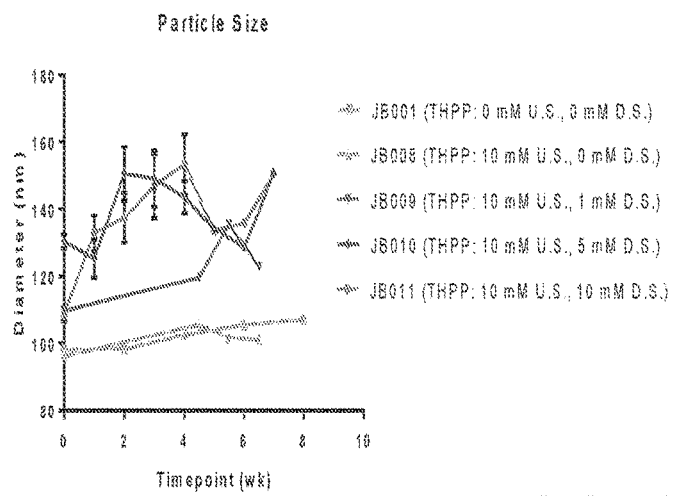
FIGS. 6(a), 6(b), and 6(c) depict the particle size (6(a)), polydispersity index (PDI) (6(b)), and zeta potential (6(c)) of SAM/LNPs formulated in the presence of the reducing agent THPP.
Figure 6B:
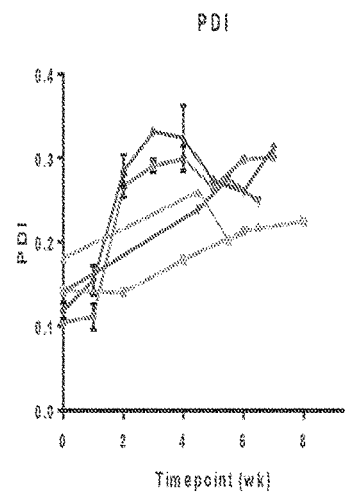
Figure 6C:
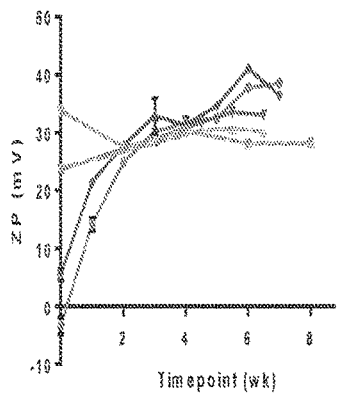

The potency of a SAM/LNP formulation in the presence of reducing agent was compared with that of a SAM/LNP formulation in a phosphate-buffered saline (PBS) control. As shown in FIG. 1, the potency of the SAM/LNP when the reducing agent was added to the SAM/LNP formulation was significantly higher than that of the SAM/LNP formulation with a PBS control (e.g. reducing agent not added to the SAM/LNP formulation). The findings of FIG. 1 were corroborated in FIG. 2(a), where the potency of several SAM/LNPs was increased when TCEP was present in both the upstream and downstream processing steps relative to if TCEP was absent from both processing steps. FIG. 2(b) further demonstrates that, when paired with TCEP, the potency of SAM/LNPs against several strains of influenza virus—H5, Bvic, H3, and H1—is increased. As shown in FIG. 3, the RNA concentration, size, encapsulation efficiency, and zeta potential of the SAM/LNPs remains stable when targeting the H5, Bvic, H3, and H1 strains of influenza virus. As shown in FIG. 4, when TCEP is present during both the upstream and downstream processing steps (green lines) the stability and potency of the SAM/LNPs is significantly increased relative to the presence of TCEP during only the upstream processing step (orange lines) or when TCEP is absent entirely (red line). In addition, as shown in FIG. 5, when TCEP is added both during the upstream and downstream processing steps (red and purple lines), the stability and potency of the SAM/LNPs is significantly increased relative to when TCEP is only added during upstream processing (yellow line) or when TCEP is absent entirely (green line).

Lastly, as shown in FIGS. 6(*a*), 6(*b*), and 6(*c*), as compared to SAM/LNPs formulated in the absence of THPP both upstream (US) and downstream (DS), SAM/LNPs formulated in the presence of 10.0 mM THPP upstream and increasing concentrations of THPP downstream (e.g., 0.0 mM, 1.0 mM, 5.0 mM and 10.0 mM) demonstrated fluctuations in particle size (6(*a*)), PDI (6(b)) and zeta potential (6(*c*)), suggesting that TCEP is a better reducing agent for SAM/LNP stability.

Although the present disclosure is described in reference to SAM/LNPs for the treatment or prevention of influenza, in various embodiments the present disclosure may include a variety of self-amplifying and non-amplifying RNA molecules for the treatment or prevention of a variety of infectious and non-diseases, including but not limited to, viral diseases, bacterial diseases, cancers, autoimmune diseases, protein-replacement therapies, cosmetics and the like.

In addition, although the present disclosure is described in reference to the use of TCEP as a reducing agent during the upstream and/or downstream SAM/LNP formulation steps, in various embodiments a variety or water-soluble neutral phosphines may be used as suitable reducing agents. Such reducing agents may generally include the beneficial attributes of being odorless, water-soluble, stable in solution, able to retain their reducing power over a broad pH range, unreactive towards other functional groups in proteins and capable of reducing disulfide bonds rapidly and completely.

REFERENCES

All references referred to are incorporated herein by reference in their entireties.

What is claimed is:

1. A method of forming a self-amplifying mRNA/lipid nanoparticle (SAM/LNP) formulation, comprising mixing first a first fluid stream containing self-amplifying mRNA molecules and second fluid stream containing a mixture of lipids under conditions such that at least a portion of the lipids of the second fluid stream form lipid nanoparticles encapsulating at least a portion of the self-amplifying molecules of the first fluid stream, wherein the first fluid or second streams further include a reducing agent.

2. The method of claim 1, wherein the reducing agent is tris(2-carboxyethyl)phosphine (TCEP).

3. The method of claim 1, wherein the first fluid stream includes citrate buffer.

4. The method of claim 1, wherein the second fluid stream includes 2,5-bis((9Z,12Z)-octadeca-9,12-dien-1-yloxy)benzyl 4-(dimethylamino)butanoate; 1,2-distearoyl-sn-glycero-3-phosphocholine; cholesterol; and DMG-PEG2000.

5. The method of claim 1, wherein the first and second fluid streams are mixed in a nanoassembler.

6. The method of claim 1, wherein the first and second fluid streams are mixed at a volume ratio of 2:1.

7. The method of claim 1, wherein the concentration of the reducing agent in the first fluid stream is 1-20 mM.

8. The method of claim 7, wherein the concentration of the reducing agent in the first fluid stream is 1-10 mM.

9. The method of claim 7, wherein the concentration of the reducing agent in the first fluid stream is 10-20 mM.

10. The method of claim 1, further comprising removing the reducing agent from the self-amplifying mRNA/lipid nanoparticle formulation.

11. The method of claim 10, wherein the reducing agent is removed by tangential flow filtration.

12. The method of claim 10, wherein substantially all of the reducing agent is removed from the self-amplifying mRNA/lipid nanoparticle formulation.

13. The method of claim 11, wherein the tangential flow filtration replaces the reducing agent with a cryobuffer.

14. The method of claim 13, further comprising re-introducing the reducing agent into the cryobuffer of the self-amplifying mRNA/lipid nanoparticle formulation.

15. The method of claim 14, wherein the reducing agent is re-introduced into the cryobuffer at a concentration of approximately 0.2 mM.

16. The method of claim 1, wherein each of the self-amplifying mRNA molecules encodes at least one influenza virus gene.

17. The method of claim 16, wherein the at least one influenza virus gene encodes epitopes from H1, H3, H5, and/or B/Victoria influenza viral strains.

18. The method of claim 14, wherein the potency of the self-amplifying mRNA/lipid nanoparticle formulation is enhanced when the reducing agent is present in both the citrate buffer and the cryobuffer as compared to the reducing agent only being present in the citrate buffer.

19. The method of claim 1, wherein the potency of the self-amplifying mRNA/lipid nanoparticle formulation is increased relative to the potency of a self-amplifying mRNA/lipid nanoparticle formulation prepared in the absence of a reducing agent.

20. The method of claim 1, wherein the potency of the self-amplifying mRNA/lipid nanoparticle formulation is increased relative to the potency of a self-amplifying mRNA/lipid nanoparticle formulation prepared and stored in the absence of a reducing agent.

21. The method of claim 14, wherein the shelf-life of the self-amplifying mRNA/lipid nanoparticle formulation is enhanced when the reducing agent is present in both the citrate buffer and the cryobuffer as compared to the reducing agent only being present in the citrate buffer.

22. The method of claim 1, wherein the shelf-life of the self-amplifying mRNA/lipid nanoparticle formulation is increased relative to the shelf-life of a self-amplifying mRNA/lipid nanoparticle formulation prepared in the absence of a reducing agent.

23. The method of claim 1, wherein the shelf-life of the self-amplifying mRNA/lipid nanoparticle formulation is increased relative to the shelf-life of a self-amplifying mRNA/lipid nanoparticle formulation prepared and stored in the absence of a reducing agent.

24. The method of claim 14, wherein the stability of the self-amplifying mRNA/lipid nanoparticle formulation is enhanced when the reducing agent is present in both the citrate buffer and the cryobuffer as compared to the reducing agent only being present in the citrate buffer.

25. The method of claim 1, wherein the stability of the self-amplifying mRNA/lipid nanoparticle formulation is increased relative to the stability of a self-amplifying mRNA/lipid nanoparticle formulation prepared in the absence of a reducing agent.

26. The method of claim 1, wherein the stability of the self-amplifying mRNA/lipid nanoparticle formulation is increased relative to the stability of a self-amplifying mRNA/lipid nanoparticle formulation prepared and stored in the absence of a reducing agent.

27. The method of claim 1, wherein the self-amplifying mRNA/lipid nanoparticle formulation is stable for at least 5 weeks at 4° C.

28. The method of claim 1, wherein the zeta potential of the self-amplifying mRNA/lipid nanoparticle formulation is stable for at least 5 weeks at 4° C.

29. The method of claim 1, wherein the encapsulation efficiency of the self-amplifying mRNA/lipid nanoparticle formulation is stable for at least 5 weeks at 4° C.

* * * * *